(12) United States Patent
Pullagurla et al.

(10) Patent No.: US 9,580,457 B2
(45) Date of Patent: Feb. 28, 2017

(54) PROCESS FOR THE PREPARATION OF (1-{9-[(4S, 2R, 3R, 5R)-3, 4-DIHYDROXY-5-(HYDROXYMETHYL) OXOLAN-2-YL)-6-AMINOPURIN-2-YL} PYRAZOLE-4-YL)-N-METHYLCARBOXAMIDE

(71) Applicant: Biophore India Pharmaceuticals PVT. Ltd., Hyderabad (IN)

(72) Inventors: Manik Reddy Pullagurla, Hyderabad (IN); Jagadeesh Babu Rangisetty, Hyderabad (IN); Mecheril Valsan Nandakumar, Hyderabad (IN)

(73) Assignee: Biophore India Pharmaceuticals PVT. Ltd., Hyderabad (IN)

( * ) Notice: Subject to any disclaimer, the term of this patent is extended or adjusted under 35 U.S.C. 154(b) by 0 days.

(21) Appl. No.: 14/438,998

(22) PCT Filed: Oct. 28, 2013

(86) PCT No.: PCT/IN2013/000654
§ 371 (c)(1),
(2) Date: Apr. 28, 2015

(87) PCT Pub. No.: WO2014/068589
PCT Pub. Date: May 8, 2014

(65) Prior Publication Data
US 2015/0353593 A1 Dec. 10, 2015

(30) Foreign Application Priority Data
Oct. 29, 2012 (IN) .......................... 4486/CHE/2012

(51) Int. Cl.
*C07H 19/22* (2006.01)
*C07H 19/16* (2006.01)
*C07H 1/00* (2006.01)
*C07H 19/167* (2006.01)

(52) U.S. Cl.
CPC .............. *C07H 19/16* (2013.01); *C07H 1/00* (2013.01); *C07H 19/167* (2013.01)

(58) Field of Classification Search
None
See application file for complete search history.

(56) References Cited

U.S. PATENT DOCUMENTS

| 7,378,400 B2 * | 5/2008 | Rieger ................... C07H 19/16 514/46 |
| 2003/0008841 A1 | 1/2003 | Devos et al. |

FOREIGN PATENT DOCUMENTS

| CN | 101012260 A | 8/2007 |
| WO | WO02070532 A2 | 9/2002 |
| WO | WO2005070947 A1 | 8/2005 |
| WO | WO2006081665 A1 | 8/2006 |
| WO | WO2006097260 A1 | 9/2006 |
| WO | WO2011020298 A1 | 2/2011 |
| WO | WO2012149196 A1 | 11/2012 |

OTHER PUBLICATIONS

Valsborg et al. Journal of Labelled Compounds and Radiopharmaceuticals (1994), vol. XXXVI, No. 5, pp. 457-464.*
Gough J. Med. Chem. (1978), vol. 21, pp. 520-525.*
Hutchinson, Scammells; Frontiers in Medical Chemistry; vol. 3, 2006; pp. 138, Synthesis of C2-Substituted Adenosines, Discloses coupling of 2, 6.
Bhalchandra V. Joshi et al. Purine Derivatives as Ligands for A3 Adenosine Receptors; Current Topics in Medicinal Chemistry, vol. 5, No. 13, Oct. 2005, pp. 1275-1295.
Palmarisa Franchetti et al. Antitumor Activity of C-Methyl- β-d-ribofuranosyladenine Nucleoside Ribonucleotide Reductase Inhibitors; J. Med. Chem., 2005,48 (15), 4983-4989 • D.
Hea O. Kim et al. 2-Substitution of N6-Benzyladenosine-5'-uronamides Enhances Selectivity for A3 Adenosine Receptors; J Med Chem. Oct. 14, 1994; 37(21): 3614-3621.
K. C. Nicolaoua et al . Synthesis and biological evaluation of 2' ,4' - and 3' ,4' -bridged nucleoside analogues, Bioorg Med Chem. Sep. 15, 2011; 19(18): 5648-5669. doi:10.101.

* cited by examiner

*Primary Examiner* — Patrick Lewis
(74) *Attorney, Agent, or Firm* — Ling Wu; Stephen Young; Ling and Yang Intellectual Property

(57) ABSTRACT

The present invention relates to a novel process for the preparation of (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

7 Claims, No Drawings

PROCESS FOR THE PREPARATION OF (1-{9-[(4S, 2R, 3R, 5R)-3, 4-DIHYDROXY-5-(HYDROXYMETHYL) OXOLAN-2-YL)-6-AMINOPURIN-2-YL} PYRAZOLE-4-YL)-N-METHYLCARBOXAMIDE

FIELD OF INVENTION

The present invention relates to a novel process for the preparation of (1-{9-[(4S,2R,3R, 5R)-3,4-dihydroxy-5-(hydroxymethyl)oxolan-2-yl)-6-aminopurin-2-yl}pyrazole-4-yl)-N-methylcarboxamide.

BACKGROUND

Regadenoson is an $A_{2A}$ adenosine receptor agonist that is a coronary vasodilator. It produces maximal hyperemia quickly and maintains it for an optimal duration that is practical for radionuclide myocardial perfusion imaging.

It was approved by the United States Food Drug Administration on Apr. 10, 2008 and is marketed by Astellas Pharma under the tradename Lexican. It has now gained approval in the European Union and is being sold in both the United Kingdom and Germany.

Regadenoson has a 2- to 3-minute biological half-life, as compared with adenosine's 30-second half-life. Regadenoson stress protocols using a single bolus have been developed, obviating the need for an intravenous line. Regadenoson stress tests are not affected by the presence of beta blockers, as regadenosonvasodilates but do not stimulate beta adrenergic receptors.

Formula I

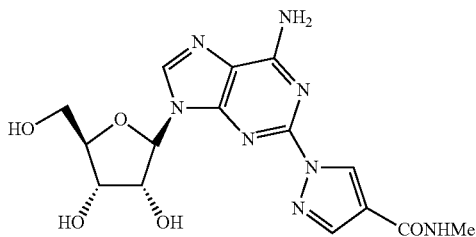

STATE OF THE ART

The following patents and applications describe the synthesis of Formula I A class of compounds possessing these desirable properties was disclosed in U.S. Pat. No. 6,403,567, the complete disclosure of which is hereby incorporated by reference. In particular, a compound disclosed in this patent, (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide, has been shown to be a highly selective $A_{2A}$ adenosine receptor agonist, and is presently undergoing clinical trials as a coronary vasodilator useful in cardiac imaging.

WO2008/143667 A1 provides the a process for the synthesis of (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide, and polymorphs thereof, preferably as its monohydrate.

Given the heightened interests in this compound, it has become desirable to find new methods of synthesis that provide a convenient method for making large quantities of the material in good yield and high purity. The patent (U.S. Pat. No. 6,403,567) provides several methods for preparing the compound. Although these methods are suitable for small scale syntheses, all synthetic methods disclosed in the patent utilize protecting groups, which is undesirable for large scale synthesis.

WO2008/143667 A1 provides the synthesis for the large scale preparation of (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide, but it involves many steps and yields are also not satisfactory.

WO2012/149196A1 provides a process for the preparation of Regadenoson by the condensation reaction of 2-chloroadenosine with 1H-pyrazole-4-carboxylic acid amide in presence of a resin based copper catalyst.

OBJECT OF THE INVENTION

One object of the invention is to develop a short possible route of synthesis of Regadenoson.

Another object of the invention is to develop a synthesis which has low amount of anomer impurity.

DETAILED DESCRIPTION OF THE INVENTION

The object of the invention was to develop shortest possible synthetic route to obtain (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

Yet another object of the invention was to develop a process devoid any anomer impurity and provide an improved method for the synthesis of (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

In one embodiment this invention provides an alternative method for preparing (1-{9-[(4S,2R,3R,5R)-3,4-dihydroxy-5-(hydroxymethyl)oxolan-2-yl)-6-aminopurin-2-yl}pyrazole-4-yl)-N-methylcarboxamide may be represented as shown in Scheme 1. Preparing 2-chloro adenosine in two steps followed by coupling with pyrazole-2-carboxamide to obtain 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

Scheme 1

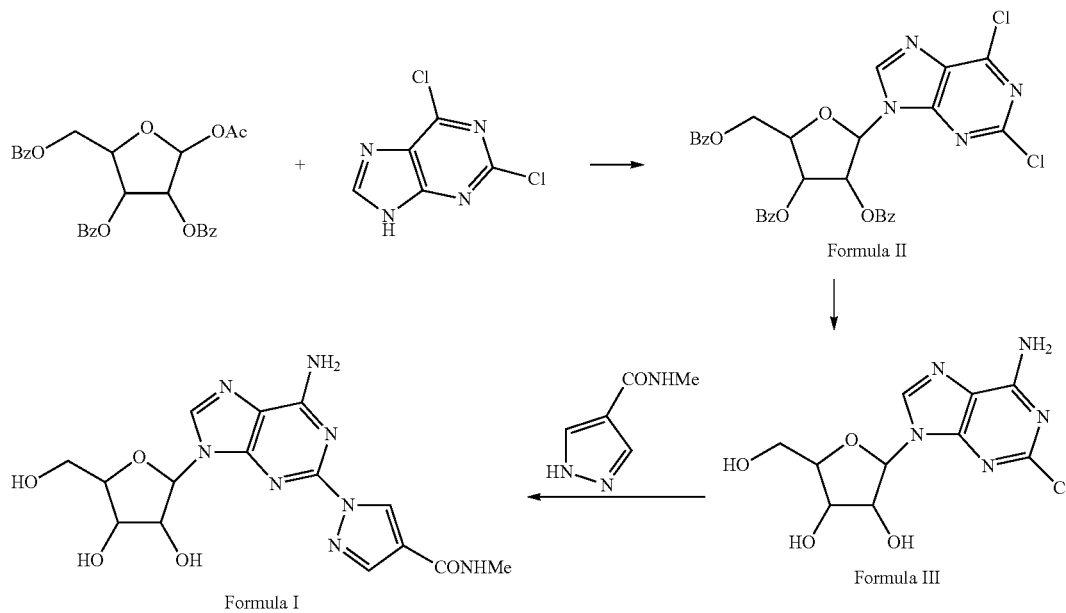

Formula I

Formula II

Formula III

Preparation of Compound of Formula II

Compound of formula II is prepared by the reaction of 2,6-dichloropurine and 1-O-acetyl-2,3,5-tri-O-benzoyl-beta-D-ribose Preparation of compound of Formula II can be carried out in presence of a Lewis acid such as $SnCl_4$, $TiCl_4$, $BBr_3$, $ZnCl_2$, TMSOTf& and also other strong acids like $H_2SO_4$& PTSA. This reaction can be carried out in acetonitrile, EDC, DMF, DMA, and Toluene, preferably in EDC or in acetonitrile at 60-100° C.

And alternatively the reaction can be carried out at 150-180° C. in absence of any solvents or Lewis acid.

The product can be isolated as apure anomer by dissolving the product in a suitable solvent, for example DMSO or protic solvents like MeOH, EtOH, IPA, t-Butanol& t-amyl alcohol.

The product is also purified by dissolving the compound in protic solvents, addition of purified water and filtering the slurry that formed & washing the solid with water followed by ethanol and drying the solid that remains under vacuum at a temperature that does not exceed 50° C.

Preparation of Compound of Formula III

The compound of Formula III is prepared by reaction of Formula II with methanolic ammonia at room temperature in a sealed pressure reactor.

Preparation of Compound of Formula I

The compound of Formula I is prepared by the condensation reaction of compound of formula III with 1H-pyrazole-4-carboxylic acid amide The reaction is carried out in presence of sodium hydride, potassium hydride &calcium hydride potassium carbonate, cesium carbonate, sodium hydroxide, potassium hydroxide, sodium bicarbonate, sodium methoxide, sodium ethoxide& potassium tertiary butoxide and preferably in presence of cesium carbonate at temperature of 25-150° C.

This reaction can be carried out in solvents like toluene, t-amyl alcohol, N-methyl-2-pyrrolidone (NMP), dimethylacetamide (DMA), dimethylformamide (DMF), dimethylsulfoxide (DMSO). Preferably in NMP or DMA.

The product obtained is purified by recrystallizations in methanol, ethanol, isopropyl alcohol or acetonitrile water mixtures.

EXAMPLE I 2,6-Dichloro-9-beta-D-(2,3,5-tri-O-benzoyl)-ribofuranosylpurine (Formula II)

10.7 g of 2,6-dichloropurine and 30 g of 1-O-acetyl-2,3,5-tri-O-benzoyl-beta-D-ribose were combined and heated to 100° C. with stirring. The reaction was allowed to stir at the same temperature until it became clear. The reaction was cooled and HOAc was removed under vacuum. Ethanol was added to the reaction and the solid isolated by filtration yielded 32 g of the crude product. The crude product was recrystallized from t-butanol to yield 28 g of 2,6-Dichloro-9-beta-D-(2,3,5-tri-O-benzoyl)-ribofuranosylpurine.

EXAMPLE II

2-Chloro-9-(beta-D-ribofuranosyl)adenine (Formula III)

A solution of Formula II (30 g) in 600 mL of methanolic ammonia was heated in an autoclave at 100° C. for 24 hours. The solution was evaporated to dryness and codistilled with methanol to remove ammonia. The residue was recrystallized from Acetone. The product was dried in vacuo at 50° C. for 12 hours to yield 14 g of 2-Chloro-9-(beta-D-ribofuranosyl) adenine as a solid.

EXAMPLE III

Method A

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in NMP is treated with potassium carbonate (1.5 eq) in a sealed reactor under an inert atmosphere. The mixture is heated at 100-150° C. for five hours and then diluted with aqueous HCl. Purification of the crude mixture by column chromatography to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide. The product was further purified by recrystallization from methanol to provide a pure compound.

Method B

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in xylene is treated with cesium carbonate (1.6 eq) in a sealed reactor under an inert atmosphere. The mixture is refluxed for 18 hours and then slurrying the crude mixture in acetonitrile to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide. The product was further recrystallized from IPA to provide a pure compound.

Method C

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in DMF is treated with sodium hydride (2 eq) in a sealed reactor under an inert atmosphere. The mixture is refluxed for 10 hours and then slurrying the crude mixture in acetone to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

Method D

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in DMA is treated with cesium carbonate in a round bottom flask under an inert atmosphere. The mixture is refluxed for 4 h and then the solvent distilled off. The crude is then slurried in acetonitrile to yield 1-{9-[(4S,2R,3R,5R)-3,4-dihydroxy-5-(hydroxymethyl)oxolan-2-yl)-6-aminopurin-2-yl}pyrazole-4-yl)-N-methylcarboxamide.

The product was further purified from DMA to provide a pure compound. The compound was recrystallized in methanol water mixtures to provide a product of >99.5% purity. Anomer content <0.15%

Method E

1-{9-[(4S,2R,3R,5R)-3,4-dihydroxy-5-(hydroxymethyl)oxolan-2-yl)-6-aminopurin-2-yl}pyrazole-4-yl)-N-methylcarboxamide (Formula I)

A solution of 2-Chloro-9-(beta-D-ribofuranosyl)adenine (1 eq) and 1H-pyrazole-4-carboxylic acid amide (1.1 eq) in NMP is treated with cesium carbonate in a round bottom flask under an inert atmosphere. The mixture is refluxed for 4 h and the solvent filtered, diluted with methanol and treated with carbon. The solvent is distilled. The crude mixture is stirred in acetonitrile to yield 1-{9-[(4S,2R,3R, 5R)-3,4-dihydroxy-5-(hydroxymethyl)oxolan-2-yl)-6-aminopurin-2-yl}pyrazole-4-yl)-N-methylcarboxamide. The product was further purified in methanol. The compound was recrystallized in methanol water mixtures to provide a product of >99.5% purity. Anomer content <0.15%

We claim:

1. A process for the preparation of Regadenoson of formula I, which comprises condensation of compound of formula III with 1H-pyrazole-4-carboxylic acid amide in the presence of a base and in the absence of copper catalysts, wherein the amide group of reactant 1H-pyrazole-4-carboxylic acid amide is not protected,

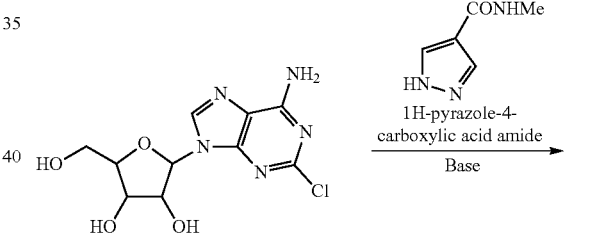

Formula III

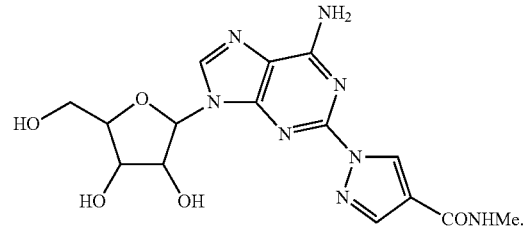

Formula I

2. The process as claimed in claim 1, wherein the base employed is selected from the group potassium carbonate, cesium carbonate, sodium hydroxide, potassium hydroxide, sodium bicarbonate, sodium methoxide, sodium ethoxide & potassium tertiary butoxide.

3. The process as claimed in claim 1, wherein the base employed is selected from sodium hydride, potassium hydride & calcium hydride.

4. The process as claimed in claim 1, wherein the reaction is carried out in solvents selected from the group toluene, t-amyl alcohol, N-methyl-2-pyrrolidone (NMP), dimethylacetamide (DMA), dimethylformamide (DMF) & dimethylsulfoxide (DMSO).

5. The process as claimed in claim 1, wherein the reaction is carried out in the presence of cesium carbonate as base and NMP as solvent at temperature ranging from 25-150° C.

6. A process for the preparation of compound of formula II

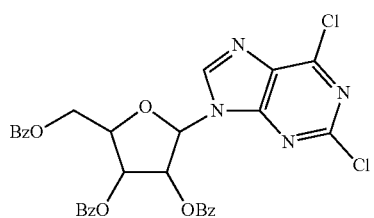

Formula II in pure anomeric form which comprises the steps of:
i) reaction of 2,6-dichloropurine and 1-O-acetyl-2,3,5-tri-O-benzoyl-beta-D-ribose optionally in the presence of Lewis acid;
ii) dissolving the obtained product in protic solvents selected from the group of methanol, ethanol, isopropyl alcohol, tertiary butanol and tertiary amyl alcohol or in an aprotic solvent DMSO;
iii) addition of purified water to above mixture and filtering the solid;
iv) drying the final product under vacuum wherein the temperature does not exceed 50° C.

7. The process as claimed in claim 6 which further involves the preparation of pure Regadenoson of formula I from anomerically pure compound of formula II,

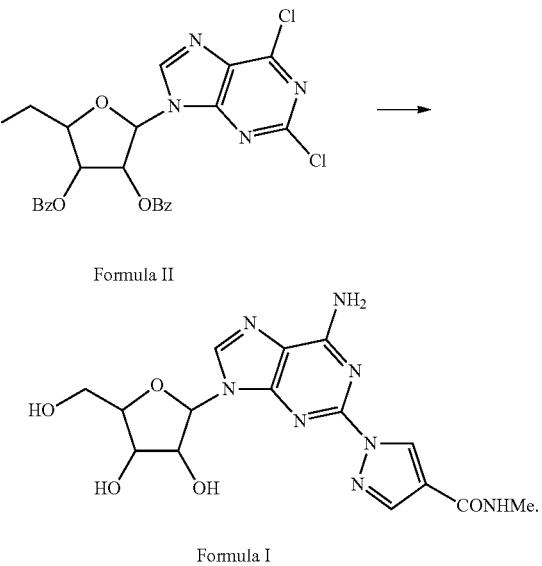

* * * * *